United States Patent
Raab et al.

(10) Patent No.: US 11,980,437 B2
(45) Date of Patent: May 14, 2024

(54) HOLDING ELEMENT FOR A DRAPE FOR A SURGICAL MICROSCOPE

(71) Applicant: Carl Zeiss Meditec AG, Jena (DE)

(72) Inventors: Andreas Raab, Neuler (DE); Frank König, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/202,914

(22) Filed: May 27, 2023

(65) Prior Publication Data

US 2023/0301739 A1    Sep. 28, 2023

Related U.S. Application Data

(63) Continuation of application No. PCT/EP2021/082928, filed on Nov. 25, 2021.

(30) Foreign Application Priority Data

Nov. 27, 2020 (DE) .................... 10 2020 131 496.5

(51) Int. Cl.
*A61B 46/10* (2016.01)
*A61B 90/20* (2016.01)

(52) U.S. Cl.
CPC .............. *A61B 46/10* (2016.02); *A61B 90/20* (2016.02)

(58) Field of Classification Search
CPC ................................ A61B 46/10; A61B 90/20
USPC ........................................................ 359/510
See application file for complete search history.

(56) References Cited

U.S. PATENT DOCUMENTS

| | | | | |
|---|---|---|---|---|
| 3,796,477 A | * | 3/1974 | Geraci | ................... A61B 46/10 359/600 |
| 5,467,223 A | * | 11/1995 | Cleveland, Jr. | .... G02B 21/0012 359/511 |
| 5,682,264 A | | 10/1997 | Cleveland et al. | |

(Continued)

FOREIGN PATENT DOCUMENTS

| CN | 102711652 A | 10/2012 |
|---|---|---|
| CN | 106890029 A | 6/2017 |

(Continued)

OTHER PUBLICATIONS

International Preliminary Report on Patentability dated Jun. 1, 2023 of international application PCT/EP2021/082928 on which this application is based and English Language Translation thereof.

(Continued)

*Primary Examiner* — Ricky D Shafer
(74) *Attorney, Agent, or Firm* — Ewers IP Law PLLC; Falk Ewers

(57) ABSTRACT

A holding element for a drape for a surgical microscope is provided. The holding element has a holding ring and a recess located in the holding ring for an interface of the surgical microscope. The holding ring has an asymmetrical contour delimiting the recess such that in a condition in which the holding element is fastened to the surgical microscope there is only one possible fastening position of the holding element on the interface of the surgical microscope that corresponds to the contour of the holding ring, in which position an orientation of the holding element relative to the surgical microscope is defined.

14 Claims, 4 Drawing Sheets

(56) References Cited

U.S. PATENT DOCUMENTS

| | | | | |
|---|---|---|---|---|
| 6,116,741 | A * | 9/2000 | Paschal | G02B 21/0012 359/511 |
| 6,902,278 | B2 | 6/2005 | Bala | |
| 10,156,718 | B2 | 12/2018 | Koenig et al. | |
| 2004/0190140 | A1 | 9/2004 | Bala | |
| 2005/0088763 | A1 * | 4/2005 | Weaver | G02B 21/0012 359/818 |
| 2006/0139753 | A1 * | 6/2006 | Moses | A61B 46/10 359/507 |
| 2007/0081243 | A1 * | 4/2007 | Fuchs | A61B 46/10 359/510 |
| 2008/0144178 | A1 * | 6/2008 | Dillon | A61B 46/10 359/510 |
| 2010/0238551 | A1 * | 9/2010 | Hubbs | G02B 27/0018 359/601 |
| 2013/0298915 | A1 | 11/2013 | Chua | |
| 2015/0002937 | A1 * | 1/2015 | Chua | A61B 46/10 359/511 |
| 2017/0168292 | A1 | 6/2017 | Koenig et al. | |
| 2021/0137626 | A1 | 5/2021 | Scholten et al. | |
| 2023/0301739 | A1 | 9/2023 | Raab et al. | |

FOREIGN PATENT DOCUMENTS

| | | |
|---|---|---|
| CN | 209747867 U | 12/2019 |
| CN | 210185719 U | 3/2020 |
| CN | 111787883 Y1 | 10/2020 |
| CN | 217112866 U | 8/2022 |
| DE | 202004021969 U1 | 10/2013 |
| DE | 102018107357 A1 | 10/2019 |
| EP | 3178438 A1 | 6/2017 |
| JP | 2017107210 A | 6/2017 |
| KR | 200429967 Y1 | 10/2006 |
| KR | 200438922 Y1 | 3/2008 |

OTHER PUBLICATIONS

International Search Report dated Mar. 3, 2022 of international application PCT/EP2021/082928 on which this application is based, and English language translation thereof.

Office Action dated Nov. 6, 2023 issued in Chinese counterpart application No. CN 202180077256.0 and English-language translations thereof.

Office Action dated Nov. 28, 2023 issued in Japanese counterpart application No. JP 2023-522546 and English-language translations thereof.

* cited by examiner

HOLDING ELEMENT FOR A DRAPE FOR A SURGICAL MICROSCOPE

CROSS REFERENCE TO RELATED APPLICATIONS

This application is a continuation application of international patent application PCT/EP2021/082928, filed Nov. 25, 2021, designating the United States and claiming priority to German patent application 10 2020 131 496.5, filed Nov. 27, 2020, and the entire content of both applications is incorporated herein by reference.

TECHNICAL FIELD

The present disclosure relates to a holding element for a drape for a surgical microscope, and to a system including the holding element and the surgical microscope.

BACKGROUND

Conventional surgical microscopes generally have a symmetrical, usually round, (main) objective, which may be covered while the surgical microscope is in operation, in particular in order to avoid contamination of the surgical microscope and/or contamination of a wound to be treated.

For covering, a sterile protective shroud or so-called sterile drape is fastened to an optical input and/or output, in particular on the objective, of the surgical microscope with a holding element with a holding ring that is fastened to the drape, in particular welded on, and the drape is then slipped or pulled over the surgical microscope and fixed to the surgical microscope, for example with adhesive tapes. The drape is generally replaced for a new one before each surgical operation, and is consequently a disposable product.

The fastening to the objective, which can be achieved for example by clamping, must be secure, in order to prevent the holding ring or the clamping ring with the drape from falling down, in particular during a surgical operation.

An objective protection glass, which may be configured as an exchangeable part, is conventionally fitted in or on the holding ring. The objective protection glass is pushed into the holding ring with guides and is held there. The objective protection glass may be aligned parallel to the objective or have a defined inclination with respect to the objective, so that reflections produced by the objective protection glass can be prevented or minimized. This makes it possible for the surgeon to have a view that is essentially free from reflections, and consequently to work ergonomically.

A disadvantage of known drapes, and in particular their holding rings, is that during mounting the holding ring can and must be freely turned on the main objective until the correct or predetermined position of the holding ring has been found.

Moreover, in addition to the main objective, further optical systems may be required, for which it is necessary in the case of conventional drapes to provide additional, separate windows or clearances for further objective protection glasses.

Furthermore, if an operator of a conventional surgical microscope finds when using the same that there are reflections too strong to allow the surgical microscope to be operated reliably, he must manually reposition a conventional holding ring. One effect of this may be that the drape becomes unsterile, and this necessitates renewed draping, i.e., renewed covering of the surgical microscope with a further drape that is still sterile. Another effect is that the repositioning may cause the drape to be pulled, and as a consequence to be damaged. This can adversely affect the procedure when carrying out a surgical operation, and should therefore be avoided.

SUMMARY

An object of the present disclosure is therefore to provide a device which is configured to overcome at least one of the disadvantages of the prior art described above.

In particular, a solution is provided that allows easier, more accurate and/or reliable positioning of a holding element of a drape on a surgical microscope and in particular prevents different optical systems of the surgical microscope from influencing one another.

According to an aspect of the disclosure, the object is achieved by a holding element for a drape for a surgical microscope, the holding element including a holding ring and a clearance, arranged in a holding ring, for an interface of the surgical microscope, a drape with a flexible portion and a holding element, and a system including a holding element for a drape and a surgical microscope as described herein.

The holding ring has a contour, delimiting the clearance.

The contour is in this case formed in such a way that, in a state in which the holding element is fastened to the surgical microscope, there is a single possible fastening position of the holding element at the interface of the surgical microscope corresponding to the contour of the holding ring. In the fastening position, an alignment of the holding element in relation to the surgical microscope is fixed.

To achieve this, the holding element is distinguished by the fact that the contour is formed so as to be asymmetrical in one portion of the contour, wherein the (asymmetrical) portion is delimited by an internal angle of at least 90°.

The contour has in the present case altogether an opening angle of 360°. That is to say that it is an encircling contour, which completely encloses the clearance. In at least one portion of the contour, which is defined or delimited by the internal angle, the contour as a whole is formed so as to be asymmetrical. In other words, the contour is formed so as to be asymmetrical over the entire portion delimited by the internal angle. That is to say that in this portion there is asymmetry not just in a small region, for example provided in the form of a clearance or groove, but the contour as such, which describes a one-dimensional set of points along an outer circumference of the clearance, is asymmetrical (in itself). It is conceivable that the contour is formed so as to be completely asymmetrical in the asymmetrical portion.

In this way, a predefined fastening position of the holding element at an interface of the surgical microscope corresponding to the contour of the holding ring can be automatically achieved during the mounting of the holding element. In particular, in this way a user can readily identify the necessary alignment of the holding element with the fastening position. Consequently, the holding element can be mounted in a particularly time-saving manner.

The internal angle may be formed in a plane which is arranged perpendicularly with respect to an axis running parallel to the fastening direction of the holding element.

For example, the asymmetrical portion may be delimited by an internal angle of at least 100°, 110°, 120°, 130°, 140°, 150°, 160°, 170°, 180°, 270°, or 360°.

"Asymmetrical" may be understood in the present case as meaning a contour delimiting the clearance that, at least in the portion delimited by the internal angle of at least 90°, optionally of at least 110°, 120°, 130°, 140°, 150°, 160°, 170°, 180°, 270° or 360°, is formed as not rotationally symmetrical, in particular not symmetrical in terms of turning, in particular not symmetrical in terms of turning with respect to the axis running parallel to the fastening direction of the holding element. It is conceivable however that the contour in this portion is formed as mirror-symmetrical. It is also conceivable however that the contour in this portion is formed as neither rotationally symmetrical nor mirror-symmetrical.

In other words, the asymmetry of the contour delimiting the clearance, i.e., the inner contour of holding ring, has the effect that the holding element centers itself in relation to a reference axis of the surgical microscope, and is laterally fixed. The holding element is spatially positioned in its axial position with an axial contact surface on the holding ring. As a result, the position of the holding element is defined in the three degrees of freedom.

Moreover, the holding ring can no longer be freely turned during or after mounting on the surgical microscope. The correct or desired position is obtained automatically. This makes it possible to avoid the need for the holding element to be repositioned, for example because of stronger reflections found during use of the surgical microscope. Consequently, unsterility of the drape caused by the repositioning, and renewed draping necessary as a result and/or damage to the drape occurring due to the repositioning, for example due to pulling on the drape, can be avoided.

The holding element described above consequently avoids disruptions that can adversely affect the procedure of a surgical operation in the case of conventional holding elements.

A drape, which may also be referred to as a protective shroud, may be understood in the present case as being a sterile disposable shroud. Such disposable shrouds are used for example in surgery for covering unsterile equipment, such as in the present case the surgical microscope, in order that there is no risk for a person wearing sterile clothing of coming into contact with unsterile surfaces by operating the equipment. The drape may be connected to the holding element by welding.

In or on the holding ring, an objective protection glass may be mounted as an exchangeable part. Through the clearance and the objective protection glass, optical inputs and/or outputs of the surgical microscope can be directed onto an operating zone. The clearance can accordingly fix a size or dimension of an optical window through which an optical axis of an optical unit of the surgical microscope passes. The clearance may also be referred to as an optical window.

The feature of "the asymmetrical contour, delimiting the clearance" may be understood in the present case as meaning that in cross section, i.e., in section in a plane to which a fastening direction of the holding element is perpendicular, the holding ring has an asymmetrical form in a region that is in contact with the interface of the surgical microscope in the state in which the holding element is fastened to the surgical microscope.

The term "ring" or "holding ring" may be understood in the present case as meaning a continuously formed object or a continuously formed device that has a clearance formed as a through-hole for the interface of the surgical microscope. An outer dimension of the through-hole or the clearance is delimited by the contour described above.

The holding ring may have a structure that is widened or widens at a predetermined angle in the fastening direction of the holding element. This widened structure may also be referred to as conical or a tapering structure.

With its asymmetrical form described above, the holding ring contains clear information for the user in terms of the direction in which the holding element is to be positioned on the surgical microscope. Furthermore, the structure widened at the angle in the fastening direction or mounting direction helps the user to position the holding element more easily.

The holding ring may have a rubber coating on its inner surface facing towards the clearance for the interface of the surgical microscope. As a result, the holding element can be fastened by static friction at the interface of the surgical microscope corresponding to the contour of the holding ring in the single possible fastening position of the holding element.

In other words, the holding ring may have in the region that is in contact with the interface of the surgical microscope in the state in which the holding element is fastened to the surgical microscope a material that allows the holding element to be fastened at the interface of the surgical microscope by static friction.

In addition, or as an alternative, the holding element may have a magnetic and/or magnetizable material for fastening the holding element to the surgical microscope. The material may be iron or an iron-containing alloy, for example.

In other words, the holding ring may be fixed or fastened at the interface of the surgical microscope by a magnetic force that acts between the surgical microscope, in particular its interface, and the holding element in the state in which the holding element is fastened to the surgical microscope.

That is to say that the fastening may take place with a rubber coating using adhesion and/or with magnets. Fastening with magnets has the advantage that it is made possible or easier for the holding ring or adapter ring to be positioned at the interface of the surgical microscope with one hand, without using additional components.

The holding ring may have a guide into which an objective protection glass can be inserted and held in the inserted state.

The guide may have a plurality of holding elements, in particular four, which are arranged and configured in such a way that the objective protection glass is fixed or fastened on the holding element in the fastening direction of the holding element. Moreover, the guide may have an element which fixes the objective protection glass in an inserting direction of the objective protection glass. The element may be configured as a latching element. In particular, a clearance in which the latching element on the objective protection glass can engage in the inserted state of the objective protection glass may be provided. Falling out of the objective protection glass while the surgical microscope is in operation can in this way be avoided.

It is conceivable that the guide is arranged and configured in such a way that the objective protection glass can be pushed into the holding ring from a direction that is arranged perpendicularly to the fastening direction. In other words, the guide can make it possible for a user to push the objective protection glass laterally into the holding ring. It is also conceivable that the guide has a stop, so that during insertion the objective protection glass can be pushed in at most as far as a predefined end point. This makes it easier for the objective protection glass to be inserted and positioned.

The guide may have an asymmetrical form, such that there is only a single possible positioning of the objective protection glass in the inserted state of the same in the holding ring, a positioning in which an alignment of the objective protection glass in relation to the holding element is fixed. This makes it even easier for the objective protection glass be inserted.

"Asymmetrical" means in the present case that the guide is formed as not rotationally symmetrical. It is conceivable however that it is formed as mirror-symmetrical. It is also conceivable however that the guide is formed as neither rotationally symmetrical nor mirror-symmetrical.

That is to say that the holding ring may have an insert into which the objective protection glass or the protective plate can be pushed and fixed. The objective protection glass and its position, in particular its skewed position or inclination, can be adapted to the surgical microscope and in particular its illumination and/or observation optical unit in such a way that disturbing or predetermined reflections in the surgical microscope and/or in a beam path of an optional observation optical unit, in particular of a tracking camera, can be avoided. It can be ensured by the inner contour of the holding ring with the asymmetry that the protective plate is correctly positioned and cannot turn.

The feature of "the asymmetrical form" of the guide may be understood in the present case as meaning that in cross section, i.e., in section in a plane to which the fastening direction of the holding element is perpendicular, the guide has an asymmetrical form or contour in a region that is in contact with the objective protection glass in the inserted state of the same.

The asymmetrical contour, delimiting the clearance, of the holding ring may have a circular portion.

In this way, and in particular together with the use of magnets described above, the holding ring may also be fastened to surgical microscopes at interfaces that do not have an asymmetrical form or do not have an interface formed as a raised portion.

It is conceivable that the holding ring has on a surface that is in contact with a surface of the interface of the surgical microscope in the state in which the holding element is fastened to the surgical microscope an elevation or a pin which for fixing engages in a corresponding clearance on the surface of the interface of the surgical microscope. The two surfaces may also be referred to in each case as a contact surface, it being possible for the fastening direction to be perpendicular to the respective contact surface.

The asymmetrical contour, delimiting the clearance, of the holding ring may have a groove. The groove may also be referred to as an elongated depression, which extends along the fastening direction of the holding element. The interface of the surgical microscope may have a projection which corresponds to the groove and engages in the groove in the state in which the holding element is fastened to the surgical microscope. As a result, a possible further form-fitting connection may be achieved for fixing the holding element at the interface of the surgical microscope.

Also provided is a drape with a flexible portion and with a holding element described above, connected to the flexible portion. The flexible portion may be a sheet, in particular a sterile sheet. The sheet may also be referred to as a protective shroud. The flexible portion may be configured in such a way that it can be fastened to an optical input and/or output of a surgical microscope with the holding ring of the holding element. It is conceivable that the flexible portion is configured in such a way that, after fastening, it can be slipped or pulled over the surgical microscope and possibly subsequently fixed on the surgical microscope.

The description above with respect to the holding element and the surgical microscope also applies analogously to the drape, and vice versa.

A system including a holding element for a drape and a surgical microscope is also provided.

The holding element has a holding ring and a clearance arranged in the holding ring for an interface of the surgical microscope.

The surgical microscope has the interface for fastening the holding element to the surgical microscope.

The holding ring has an asymmetrical contour, delimiting the clearance.

The interface has an asymmetrical contour which outwardly delimits the interface and which, in a state in which the holding element is fastened to the surgical microscope, is in contact with the asymmetrical contour, delimiting the clearance, of the holding ring.

The asymmetrical contour, delimiting the clearance, of the holding ring corresponds to the asymmetrical contour, outwardly delimiting the interface, of the interface of the surgical microscope in such a way that, in the state in which the holding element is fastened to the surgical microscope, there is a single possible fastening position of the holding element on the asymmetrical contour, outwardly delimiting the interface, of the interface of the surgical microscope. In the fastening position, an alignment of the holding element in relation to the surgical microscope is fixed.

The system may include the holding element described above, it being possible for the holding element to be connected to the drape. The description above with respect to the holding element, the drape and the surgical microscope also applies analogously to the system including the holding element and the surgical microscope. In particular, the holding element may be fastened at the interface of the surgical microscope.

The interface of the surgical microscope may have at least two optical inputs and/or outputs. The clearance, arranged in the holding ring, for the interface of the surgical microscope may be dimensioned in such a way that the at least two optical inputs and/or outputs of the surgical microscope are arranged within the clearance in the state in which the holding element is fastened to the surgical microscope.

In other words, in addition to an optical input and/or output, in particular for a main optical unit of the surgical microscope, it may be necessary that the surgical microscope has a further or additional optical input and/or output. In order to avoid interaction or mutual influencing of the individual optical inputs and/or outputs, it may also be necessary to place them away from one another, but as close as possible to an optical axis of the main optical unit.

The main optical unit may be an objective with a fixed or variable focal length. In particular, a movable displaceable optical unit is conceivable.

The fact that the clearance for the interface of the surgical microscope that is arranged in the holding ring can be dimensioned in such a way that the at least two optical inputs and/or outputs of the surgical microscope are arranged within the clearance in the state in which the holding element is fastened to the surgical microscope means that a shared optical window can be formed for the single or multiple optical input and/or outputs on the surgical microscope. The optical axes of multiple or all optical inputs and/or outputs can consequently pass through the optical window defined by the clearance.

That is to say that in the present case it may be sufficient if a single objective protection glass is provided for the at least two optical inputs and/or outputs. It can in this way be prevented that the optical inputs and/or outputs influence one another by reflections due to different angles or positionings of the objective protection glasses, as may be the case with conventional systems. Furthermore, an incorrect positioning, which may occur with conventional systems including multiple individual windows, can be avoided.

It is conceivable that one of the at least two optical inputs and/or outputs is intended for a (main) optical unit of the surgical microscope, and the second of the at least two optical inputs and/or outputs is intended for an illumination element, which is in particular configured to emit light at a predetermined wavelength, a camera system and/or a system for superimposing at least one item of information into an operating area.

In other words, the additional optical input or inputs and/or output or outputs may be provided to make further applications possible on the surgical microscope in addition to the main optical unit, such as for example illumination at a specific wavelength, which may be required in conjunction with filters for visualization, the provision of a camera system and/or the superimposing of a structure into the operating area or the operating zone.

The system may have an objective protection glass, in particular with a coating. The coating may be an antireflection coating, which may be configured to suppress reflection at the objective protection glass and optionally increase its transmission.

The holding ring may, as described above, have a guide into which the objective protection glass can be inserted and held in the inserted state.

This guide of the holding ring may have an asymmetrical form, such that there is only a single possible positioning of the objective protection glass in the inserted state of the same in the holding ring, a positioning in which an alignment of the objective protection glass in relation to the holding element is fixed.

The guide of the holding ring and/or the objective protection glass may be formed in such a way that the objective protection glass in the inserted state of the same in the holding element is arranged parallel to or inclined at a predetermined angle in relation to the interface of the surgical microscope.

As a result, an alignment of the objective protection glass can be adapted to the surgical microscope in such a way that any reflections occurring that are disturbing for a user of the surgical microscope can be minimized.

BRIEF DESCRIPTION OF THE DRAWINGS

The disclosure will now be described with reference to the drawings wherein.

DESCRIPTION OF EXEMPLARY EMBODIMENTS

Figure 1:
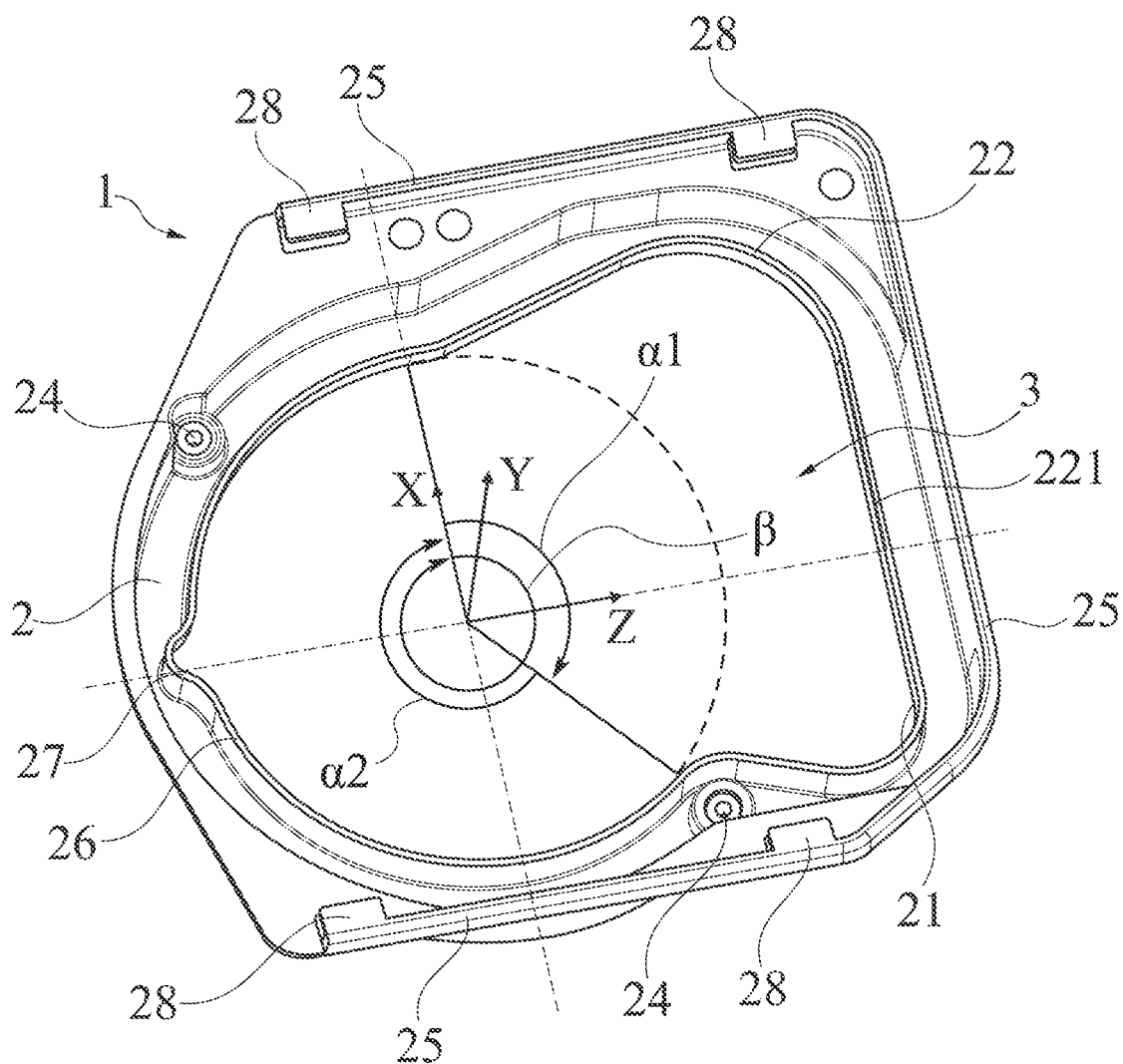
FIG. 1 shows a perspective view of a side of a holding element that is facing away from a surgical microscope according to an exemplary embodiment of the disclosure.
Figure 3:
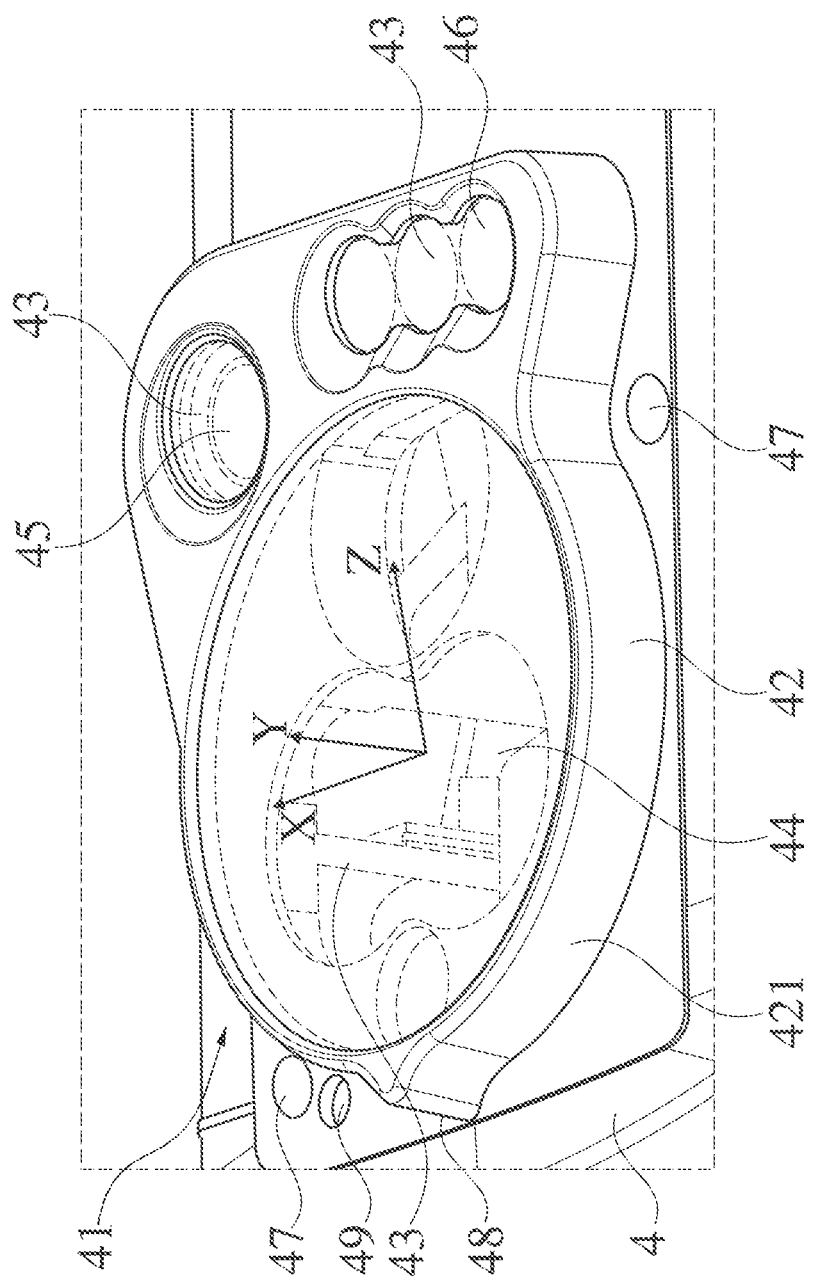
FIG. 3 shows a perspective view of an interface of the surgical microscope that is intended for the holding element from FIGS. 1 and 2 according to the exemplary embodiment of the disclosure.
Figure 4:
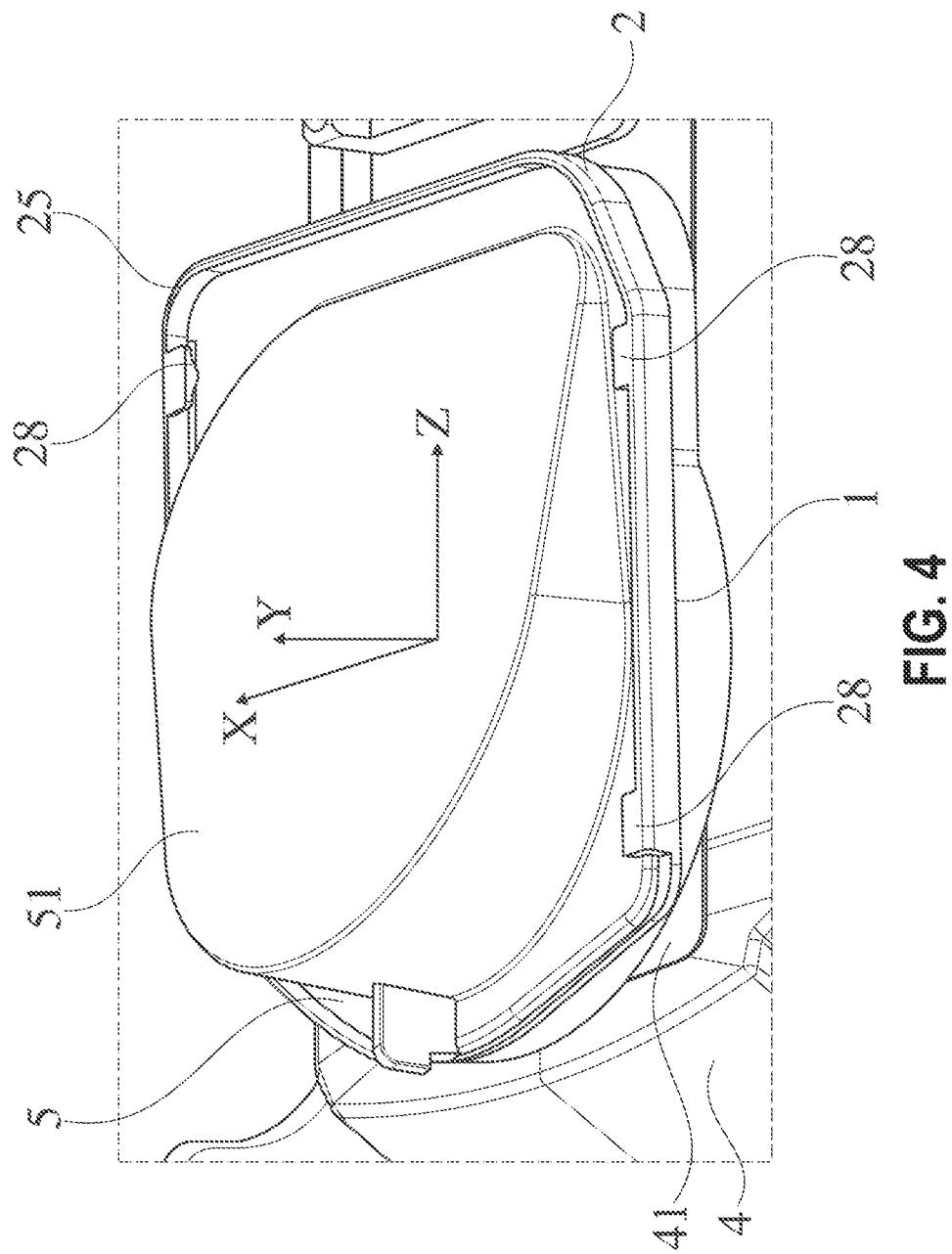
FIG. 4 shows a perspective view of the holding element shown in FIGS. 1 and 2 that is mounted at the interface shown in FIG. 3.

Shown in FIG. 1 is a holding element 1 for a drape (not shown) for a surgical microscope 4 (see FIGS. 3 and 4).

The side of the holding element 1 shown in FIG. 1 is the side that is facing away from the surgical microscope 4 and facing towards an operating area in a state in which the holding element 1 is fastened to the surgical microscope 4. This side of the holding element 1 is referred to below as the front side.

Figure 2:
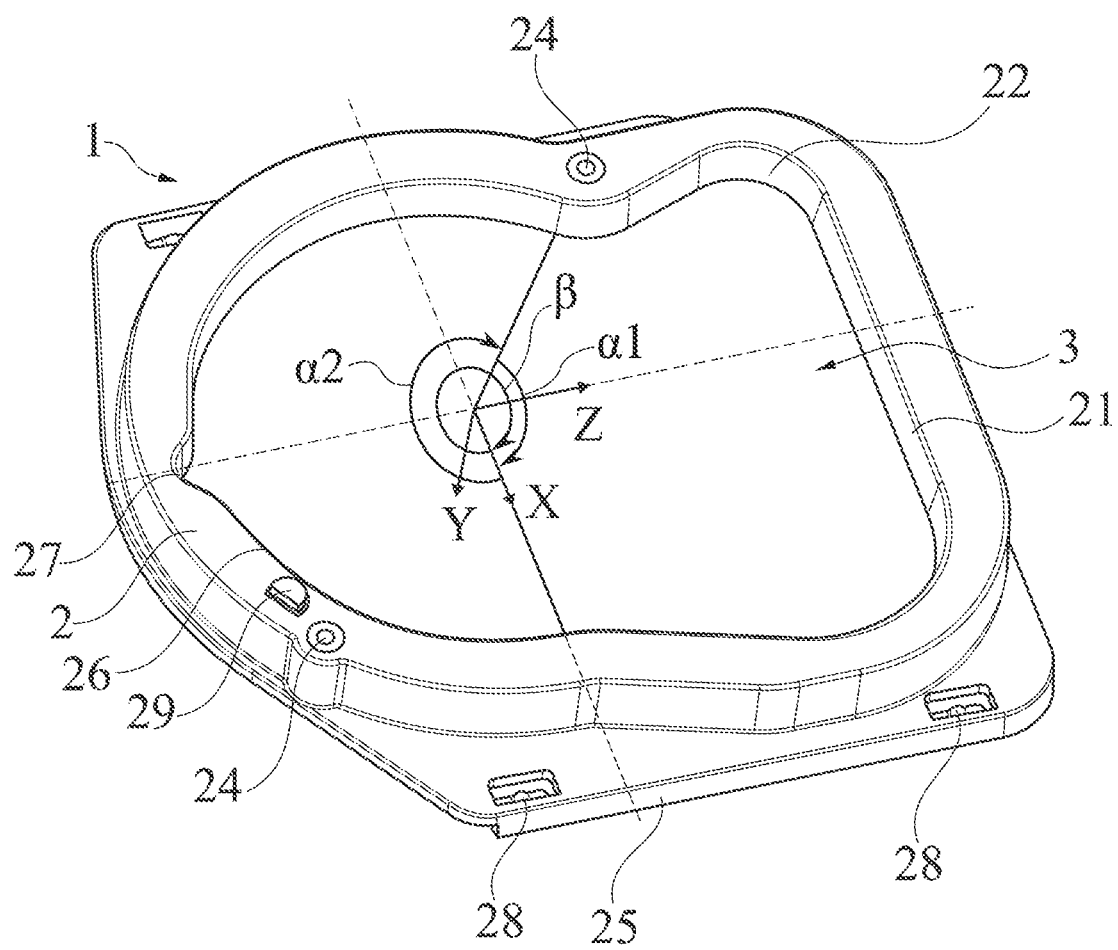
FIG. 2 shows a perspective view of a side of the holding element from FIG. 1 that is facing towards the surgical microscope.

In FIG. 2, the holding element 1 is likewise shown. The side of the holding element 1 that is shown in FIG. 2 is the side that is facing towards the surgical microscope 4 and in contact with an interface 41 of the surgical microscope 4 in a state in which the holding element 1 is fastened to the surgical microscope 4 (see also FIGS. 3 and 4).

This side of the holding element 1 consequently forms a contact surface on the interface 41 of the surgical microscope 4 and is referred to below as the rear side.

Also shown in FIGS. 1 and 2 is a Cartesian coordinate system, the y-axis of the coordinate system corresponding to a mounting or fastening direction of the holding element 1 at the interface 41 of the surgical microscope 4. The rear side is opposite the front side in the fastening direction Y of the holding element 1.

The holding element 1 has a holding ring 2 and a clearance 3, arranged in the holding ring 2, for the interface 41 of the surgical microscope 4 (see also FIG. 3). The clearance 3 is configured as a through-hole and extends from the front side to the rear side of the holding element 1.

In FIG. 3, the interface 41 of the surgical microscope 4 is shown. Also shown in FIG. 3, as in FIGS. 1 and 2, is the Cartesian coordinate system, with here too the y-axis of the coordinate system corresponding to the mounting or fastening direction of the holding element 1 at the interface 41 of the surgical microscope 4.

For the mounting or fastening of the holding element 1, it is pushed along the fastening direction Y onto the interface 41, such that a surface 421, which outwardly delimits the interface 41 in the X direction and Z direction and has an asymmetrical contour 42, is in contact with a surface 22 of the holding ring 2 which outwardly delimits the clearance 3 of the holding element 1 in the X direction and Z direction and likewise has an asymmetrical contour 21. These two surfaces 22, 421 form a form fit after mounting.

The contour 21 completely encloses the clearance 3 formed in the holding ring 2, and therefore has in FIG. 1 an opening angle β of 360°, which in the present case is arranged in a plane which is defined by the X direction or X axis and the Z direction or Z axis and to which the fastening direction Y is perpendicular.

The contour 21 can be subdivided substantially into two portions, with an internal angle α1 of substantially 140° and an internal angle α2 of substantially 220°, which correspond in total to the opening angle β of 360°, wherein the internal angles α1, α2 are respectively formed in the plane defined by the X axis and the Z axis.

In the portion which is defined or delimited by the internal angle α1, and consequently forms a contiguous portion of altogether substantially 140°, the contour 21 as a whole is formed so as to be asymmetrical. That is to say that, although the contour 21 has in the region defined by the internal angle α1 individual subportions which are mirror-symmetrical and/or rotationally symmetrical (for example the straight-running portion 211 of the contour 21 that is arranged on the right in FIG. 1 is at least partially axisymmetrical with respect to the Z axis), the contour 21 as a whole is not symmetrical in the region defined by the internal angle α1. The asymmetry as a whole consequently relates in the present case to the entire progression of the contour 21 in the region defined by the internal angle α1, wherein this entire progression has a lack of rotational symmetry with respect to each axis running parallel to the fastening direction Y, and here also a lack of axisymmetry with respect to each axis that is arranged completely in the plane defined by the X axis and the Y axis.

In the further portion of the contour 21 that is defined by the internal angle α2, the contour 21 is formed so as to be substantially circular, and consequently substantially rotationally symmetrical with respect to the Y axis, by a circular portion 26 (a circle indicated by a dashed line in FIG. 1). The further portion of the contour 21 that is defined by the internal angle α2 is consequently substantially (rotationally) symmetrical as a whole. Not detracting from this is the fact that the contour 21 in the present case has in a small region an asymmetry or an asymmetrical location in the form of a groove 27. It is conceivable that the asymmetrical location, here the groove 27, is formed in an angular range of at most 30°, typically between 20° and 30°, more typically of 26°. The asymmetrical configuration of both the outer surface 421 of the interface 41 and the inner surface 22 of the holding ring 2, which as described above have in each case the contour 21, 42—which is asymmetrical in particular in the portion α1—in the region that is in contact with the respective other component after mounting, means that a predefined fastening position of the holding element 1 to the surgical microscope 4 is automatically achieved during the mounting of the holding element 1. In particular, the fact that, in a region of at least 90°, in the present case substantially 140°, the contour 21 is formed so as to be asymmetrical as a whole means that the predefined fastening position of the holding element 1 to the surgical microscope 4 is ensured during the mounting in an ergonomically easy way that could not be achieved by the formation of an asymmetrical location, such as the groove 27, alone.

That is to say that, in the state in which the holding element 1 is fastened to the surgical microscope 4, there is only a single possible fastening position of the holding element 1 at the interface 41 of the surgical microscope 4 corresponding to the contour 21 of the holding ring 2. In this fastening position, an alignment of the holding element 1 in relation to the surgical microscope 4 is spatially fixed.

This makes it easier for an operator of the surgical microscope 4 to mount the holding element 1 correctly in a relatively short period of time.

In order to further enhance the effect of easier and therefore more ergonomic mounting of the holding element 1 achieved by the configuration of the holding element 1 and the interface 41 of the surgical microscope 4, the holding ring 2 has a structure 22 which is widened or conical at a predetermined angle in the fastening direction Y of the holding element 1. The interface 41 of the surgical microscope 4 that is shown in FIG. 3 likewise has for this a structure 421 that is widened at a predetermined angle. This structure 421 formed at the interface 41 may also be referred to as an insertion bevel and corresponds to the structure 22 that is widened at the predetermined angle of the holding ring 2.

For mounting or fastening the holding element 1 at the interface 41 of the surgical microscope 4, the holding element 1 is placed on the interface 41 and pushed onto the interface 41 along the fastening direction Y, so that the respective widened structures 22, 421 are in contact with one another. This allows guided mounting of the holding element 1 on the surgical microscope 4 to be realized, in particular until the fastening position of the holding element 1 is reached.

In order to make easier positioning of the holding element 1 possible during the mounting of the same even at interfaces (not shown) that have a substantially circular contour and not an asymmetrical contour, the asymmetrical contour 21, delimiting the clearance 3, of the holding ring 2 has a circular portion 26 for the centering of the holding element 1. Moreover, formed on the contact surface or the rear side of the holding ring 2 is an elevation 29, which engages in a corresponding depression 49 at the interface 41 in the state in which the holding element 1 is mounted on the interface 41, in order to secure the holding element 1 against turning in relation to the interface 41 (see in particular FIGS. 2 and 3).

As described above, the holding ring 2 has the groove 27 in the circular portion 26. A protruding portion 48 of the interface 41 may engage in this groove 27.

The end position or fastening position with the holding element 1 fastened or mounted on the interface 41 is shown in FIG. 4. In this position, the interface 41 and the holding ring 2 are connected to one another in a form-fitting manner.

To be more precise, in FIG. 4 the interface 41 of the surgical microscope 4 is shown with the holding element 1 mounted or fastened on it. Also shown in FIG. 4, as in FIGS. 1, 2, and 3, is the Cartesian coordinate system, with here too the y-axis of the coordinate system corresponding to the mounting or fastening direction of the holding element 1 at the interface 41 of the surgical microscope 4.

In order that the holding element 1 can be held at the interface 41 of the surgical microscope 4, there are two conceivable configurations of the holding element 1 and the interface 41, which may be provided as alternatives or in combination.

Accordingly, the holding ring 2 may have a rubber coating on its inner surface 22, facing the clearance 3 for the interface 41 of the surgical microscope 4.

This rubber coating is provided at least in the region of the holding ring 2 that is in contact with the interface 41 in the fastening position, i.e., in particular in the region in which the widened structure 22 is formed on the holding ring 2. In the present case, this region adjoins the rear side of the holding element 1.

The rubber coating allows the holding element 1 to be fastened and held by static friction, produced by a clamping force between the holding ring 2 and the interface 41, in the single possible fastening position of the holding element 1 at the interface 41 of the surgical microscope 4 corresponding to the contour 21 of the holding ring 2.

This configuration is also conceivable oppositely, i.e., in addition or as an alternative the interface 41 may also have a rubber coating in the region 421 that is in contact with the holding ring 2 in the fastening position of the same.

In addition, or as an alternative to the rubber coating, the holding element 1 may have a magnetic material 24 for the fastening of the holding element 1 at the interface 41 of the surgical microscope 4.

It is in this case conceivable that a magnetic material 24 is arranged at a number of places on the holding ring 2, in the present case at two places (see FIG. 1). At the places on the interface 41 that correspond to the place or places at which the magnetic material 24 is arranged on the holding ring 2, a magnetic material 47 may likewise be arranged. The holding element 1 may be fastened at the interface 41 of the surgical microscope 4 and held there by magnetic forces acting between the magnetic materials 24, 47.

Also shown in FIG. 4 is the objective protection glass 5 pushed into a guide 25 attached to the holding ring 2 of the holding element 1. This glass is held in the fastening direction Y by the guide 25, so that falling out of the objective protection glass 5 in the direction of the operating area is avoided. For this purpose, the guide 25 has at least one holding element or guiding element 28 for the objective protection glass 5, in the present case four holding or guiding elements 28 arranged on the guide 25, for the objective protection glass 5 (see in particular FIG. 1), which hold the objective protection glass 5 in the inserted state For inserting the objective protection glass 5, it is pushed laterally, here along the Z direction, into the guide 25, in particular after the mounting of the holding element 1 at the interface 41. The guide 25 has an (end) stop in the inserting direction Z of the objective protection glass 5, so that an end position of the objective protection glass 5 in the inserting direction Z is fixed.

Furthermore, the holding or guiding elements 28 have in each case integrated latching elements for the objective protection glass 5 (see in particular FIG. 2), such that the objective protection glass 5 is prevented from falling out or sliding out against the inserting direction Z while the surgical microscope 4 is in operation. The holding or guiding elements 28 with integrated latching make it possible, in addition to the fixing of the objective protection glass 5 in its end position, for the objective protection glass 5 to be guided in a play-free manner.

Every two of the four holding or guiding elements 28, together with a side surface on the left or right (i.e., opposite one another on the x-axis) of the guide 25 and a bearing surface on the holding ring 2, to which the fastening direction Y is perpendicular, form a longitudinal groove for guiding the objective protection glass 5.

In the same way as the interface 41 and the holding ring 2, the guide 25 and also the objective protection glass 5 have an asymmetrical form, so that there is only a single possible positioning of the objective protection glass 5 in the inserted state of the same in the holding ring 2. In the inserted state of the objective protection glass 5, an alignment of the objective protection glass 5 in relation to the holding ring 2 is fixed. In this way, an alignment of the objective protection glass 5 in relation to the surgical microscope 4 is also fixed.

In the present case, the interface 41 of the surgical microscope 4 has three optical inputs and/or outputs 43. One of the three optical inputs and/or outputs 43 is intended for a (main) optical unit 44 of the surgical microscope 4. The two other inputs and/or outputs 43 of the three are intended for an illumination element 46, which is configured in particular to emit light at a predetermined wavelength, and a camera system 45. A fourth optical input and/or output 43 would be conceivable, intended for a system for superimposing at least one item of information into an operating area.

The clearance 3, arranged in the holding ring 2, for the interface 41 of the surgical microscope 4 is dimensioned in such a way that the three optical inputs and/or outputs 43 of the surgical microscope 4 are arranged within the clearance 3 in the state in which the holding element 1 is fastened to the surgical microscope 4.

It is therefore sufficient to provide a single objective protection glass 5 for the three optical inputs and/or outputs 43.

It can among other things be prevented in this way that the optical inputs and/or outputs 43 influence one another by reflections due to different angles or positionings of the objective protection glasses. Furthermore, incorrect positioning that may occur with conventional systems including multiple individual windows can be avoided.

As can be seen from FIG. 4, the objective protection glass 5 is formed in the present case in such a way that a surface 51 of the objective protection glass 5 facing towards the operating area in the inserted state of the same in the holding element 1 is arranged inclined at a predetermined angle in relation to the interface 41 of the surgical microscope 4.

It would also be conceivable that the inclination of the objective protection glass 5 is produced by a corresponding structural configuration of the guide 25.

By providing the inclination, the advantage described above of avoiding reflections can be further enhanced. It is also conceivable that the objective protection glass 5, and, in particular, its surface 51 facing towards the operating area, has for this purpose an antireflection coating.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Holding element for drape
2 Holding ring
21 Asymmetrical contour, delimiting the clearance
211 Axisymmetrical portion
22 Surface on the holding ring, with structure widened in fastening direction, with rubber coating
24 Magnetic material
25 Guide for objective protection glass with end stop in inserting direction
26 Circular portion of the contour
27 Groove in the contour delimiting the clearance
28 Holding or guiding element(s) for the objective protection glass
29 Elevation or protruding portion on the holding ring
3 Clearance for interface of the surgical microscope
4 Surgical microscope
41 Interface for holding element
42 Asymmetrical contour, outwardly delimiting the interface
421 Surface at interface with structure widened in fastening direction
43 Optical inputs and/or outputs of the surgical microscope
44 (Main) optical unit of the surgical microscope
45 Camera system
46 Illumination element
47 Magnetic material
48 Protruding portion at interface for groove on the holding ring
49 Depression at interface corresponding toelevation at the holding ring
5 (Exchangeable) objective protection glass
51 Surface of the objective protection glass facing towards the operating area
$\alpha 1$, $\alpha 2$ Internal angle of the contour delimiting the clearance
$\beta$ Opening angle of the contour delimiting the clearance

What is claimed is:

1. A holding element for a drape for a surgical microscope, the holding element comprising:
a holding ring; and
a clearance arranged in the holding ring for an interface of the surgical microscope,
wherein the holding ring has an asymmetrical contour, delimiting the clearance, wherein the asymmetrical contour has an asymmetrical form in terms of turning with respect to an axis running parallel to a fastening direction of the holding element in at least one portion of the contour, wherein the at least one portion is delimited by an internal angle of at least 90°, such that, in a state in which the holding element is fastened to the surgical microscope, there is a single possible fastening position of the holding element at the interface of the surgical microscope corresponding to the asymmetrical contour of the holding ring in which an alignment of the holding element in relation to the surgical microscope is fixed, and wherein the holding ring has a structure which is widened at a predetermined angle in the fastening direction of the holding element.

2. The holding element according to claim 1, wherein the holding ring has a rubber coating on its inner surface facing towards the clearance for the interface of the surgical microscope, such that the holding element can be fastened by static friction at the interface of the surgical microscope corresponding to the asymmetrical contour of the holding ring in the single possible fastening position of the holding element.

3. The holding element according to claim 1, wherein the holding element has at least one of a magnetic and magnetizable material for fastening the holding element to the surgical microscope.

4. The holding element according to claim 1, wherein the holding ring has a guide, into which an objective protection glass can be inserted and held in an inserted state.

5. The holding element according to claim 4, wherein the guide has an asymmetrical form, such that there is only a single possible positioning of the objective protection glass in the inserted state of the same in the holding ring, a positioning in which an alignment of the objective protection glass in relation to the holding element is fixed.

6. The holding element according to claim 1, wherein the asymmetrical contour, delimiting the clearance, of the holding ring has at least one circular portion.

7. The holding element according to claim 1, wherein the asymmetrical contour, delimiting the clearance, of the holding ring has a groove.

8. The drape, comprising:
a flexible portion; and
a holding element according to claim 1, wherein the holding element is connected to the flexible portion.

9. A system, comprising:
a holding element for a drape; and
a surgical microscope having an interface for fastening the holding element to the surgical microscope,
wherein the holding element has a holding ring and a clearance, arranged in the holding ring, for the interface of the surgical microscope,
wherein the holding ring has an asymmetrical contour, delimiting the clearance, wherein the asymmetrical contour has at least one portion which has an asymmetrical form in terms of turning with respect to an axis running parallel to a fastening direction of the holding element, wherein the at least one portion is delimited by an internal angle of at least 90 degrees, and wherein the interface has an asymmetrical contour which outwardly delimits the interface and which, in a state in which the holding element is fastened to the surgical microscope, is in contact with the asymmetrical contour, delimiting the clearance, of the holding ring, and wherein the asymmetrical contour delimits the clearance, corresponding to the asymmetrical contour, which outwardly delimits the interface, such that, in the state in which the holding element is fastened to the surgical microscope, there is a single possible fastening position of the holding element at the interface in which an alignment of the holding element in relation to the surgical microscope is fixed.

10. The system according to claim 9, wherein the holding element is connected to a flexible portion of a drape.

11. The system according to claim 9, wherein the interface of the surgical microscope has at least two optical inputs, outputs or both, and the clearance, arranged in the holding ring, for the interface of the surgical microscope is dimensioned such that the at least two optical inputs, outputs or both of the surgical microscope are arranged within the clearance in the state in which the holding element is fastened to the surgical microscope.

12. The system according to claim 11, wherein one of the at least two optical inputs, outputs or both is provided for an optical unit of the surgical microscope, and a second of the at least two optical inputs, outputs or both is provided for an illumination element, which is configured to emit light at a predetermined wavelength, a camera system or a system for superimposing at least one item of information into an operating area.

13. The system according to claim 9, wherein:
the system further comprises an objective protection glass with a coating,
the holding ring has a guide into which the objective protection glass can be inserted and held in an inserted state of the same, and
the guide of the holding ring has an asymmetrical form, such that there is only a single possible positioning of the objective protection glass in the inserted state of the objective protection glass in the holding ring, a positioning in which an alignment of the objective protection glass in relation to the holding element is fixed.

14. The system according to claim 13, wherein the guide of the holding ring and/or the objective protection glass is formed such that the objective protection glass in the inserted state of the same in the holding element is arranged parallel to or inclined at a predetermined angle in relation to the interface of the surgical microscope.

\* \* \* \* \*

UNITED STATES PATENT AND TRADEMARK OFFICE
CERTIFICATE OF CORRECTION

PATENT NO. : 11,980,437 B2
APPLICATION NO. : 18/202914
DATED : May 14, 2024
INVENTOR(S) : Andreas Raab and Frank König It is certified that error appears in the above-identified patent and that said Letters Patent is hereby corrected as shown below:

In the Claims

For Claim 14, Column 14,
Line 51: Replace "and/or" with "or"

Signed and Sealed this
Seventeenth Day of September, 2024

Katherine Kelly Vidal
*Director of the United States Patent and Trademark Office*